United States Patent
Baiera et al.

(10) Patent No.: US 11,120,915 B2
(45) Date of Patent: *Sep. 14, 2021

(54) EVIDENCE ANALYSIS AND PRESENTATION TO INDICATE REASONS FOR MEMBERSHIP IN POPULATIONS

(71) Applicant: International Business Machines Corporation, Armonk, NY (US)

(72) Inventors: James C. Baiera, Medina, OH (US); Jill R. Doty, Cleveland, OH (US); Daniel Kim, Cleveland, OH (US); David A. Kwasny, Ravenna, OH (US); Douglas S. Meil, Chagrin Falls, OH (US)

(73) Assignee: International Business Machines Corporation, Armonk, NY (US)

( * ) Notice: Subject to any disclaimer, the term of this patent is extended or adjusted under 35 U.S.C. 154(b) by 1258 days.

This patent is subject to a terminal disclaimer.

(21) Appl. No.: 15/064,071

(22) Filed: Mar. 8, 2016

(65) Prior Publication Data
US 2017/0262612 A1 Sep. 14, 2017

(51) Int. Cl.
*G16H 50/70* (2018.01)

(52) U.S. Cl.
CPC .................. *G16H 50/70* (2018.01)

(58) Field of Classification Search
USPC ........................................................ 705/2–4
See application file for complete search history.

(56) References Cited

U.S. PATENT DOCUMENTS

| 8,038,613 B2* | 10/2011 | Stupp | G16H 20/60 600/300 |
| 8,589,187 B2* | 11/2013 | Gillam | G16H 50/30 705/3 |
| 8,898,798 B2 | 11/2014 | Rogers et al. | |
| 2008/0162182 A1* | 7/2008 | Cazares | G16H 40/67 705/2 |

(Continued)

FOREIGN PATENT DOCUMENTS

EP 3370175 A1 * 9/2018 ............. G06F 19/00

OTHER PUBLICATIONS

Pathak, Jyotishman et al. "Normalization and standardization of electronic health records for high-throughput phenotyping: the SHARPn consortium." Journal of the American Medical Informatics Association : JAMIA vol. 20,e2 (2013): e341-8. doi:10.1136/amiajnl-2013-001939. (Year: 2013).*

(Continued)

*Primary Examiner* — Mark Holcomb
(74) *Attorney, Agent, or Firm* — Will Stock; Edell, Shapiro & Finnan, LLC

(57) ABSTRACT

A method, a machine-readable storage medium and at least one processing device are provided for analyzing and tracking results of multiple conditions associated with a population criteria, which is evaluated for each entity of at least one entity. The at least one processing device performs analytics associated with the population criteria, which is evaluated for each entity. Results of the analyzing of the multiple conditions are selectively tracked by the at least one processing device. The at least one processing device presents the tracked results to indicate a status of the at least one entity with respect to the tracked analytics.

10 Claims, 13 Drawing Sheets

(56) References Cited

U.S. PATENT DOCUMENTS

| | | | | |
|---|---|---|---|---|
| 2008/0177567 A1* | 7/2008 | Friedlander | ............ | G06Q 40/08 |
| | | | | 705/2 |
| 2008/0275729 A1* | 11/2008 | Taggart | ................ | G16H 50/20 |
| | | | | 705/2 |
| 2009/0076845 A1* | 3/2009 | Bellin | ................... | G06Q 10/10 |
| | | | | 705/2 |
| 2014/0032240 A1 | 1/2014 | Lougheed et al. | | |
| 2014/0297324 A1 | 10/2014 | Duftler et al. | | |
| 2015/0193583 A1* | 7/2015 | McNair | ................ | G16H 50/20 |
| | | | | 705/2 |
| 2015/0317337 A1 | 11/2015 | Edgar | | |

OTHER PUBLICATIONS

Wyrwich, Kathleen W., William M. Tierney, and Fredric D. Wolinsky. "Further evidence supporting an SEM-based criterion for identifying meaningful intra-individual changes in health-related quality of life." Journal of clinical epidemiology 52.9 (1999): 861-873. (Year: 1999).*

Coste et al.; Ttl: A population-based analytical approach to assessing patterns, determinants, and outcomes of health care with application to ectopic pregnancy; Publication Ttl: Medical Care, vol. 38, No. 7, pp. 739-749; 2000; Publisher: Lippincott Williams &Wilkins; Country of Publication: USA; ISSN:0025-7079; Database: SciSearch.

Raths; Ttl: Healthcare analytics: Moving from Setup to Use Cases. Pioneer patient care organizations are moving rapidly to leverage analytics for population health and accountable care; Publication Ttl: Healthcare Informatics, vol. 32, No. 4, pp. 58(3); Jul. 2015; Publisher: Vendome Group LLC; Country of Publication: USA; ISSN:1050-9135; Database: Gale Group, 4 pages.

"The Explorys Platform", IBM Watson Health, Solution Brief, Produced in the United States of America, Nov. 2015, 4 pages.

List of IBM Patents or Patent Applications Treated as Related, Jul. 2017, 1 page.

T. Tran, et al., "Learning vector representation of medical objects via EMR-driven nonnegative restricted Boltzmann machines (eNRBM)", Journal of Biomedical Informatics 54 (2015) 96-105, 10 pages.

* cited by examiner

802 ⎰ <DenominatorDescription>Patients ages 51-75 years at
    ⎱ the end of the measurement period.</DenominatorDescription>

804 ⎰ <NumeratorDescription>One or more screenings for
    ⎟ colorectal cancer. Any of the following meet criteria: * Fecal
    ⎟ occult blood test during the measurement period. * Flexible
    ⎨ sigmoidoscopy during the measurement period or the four years
    ⎟ prior to the measurement period. * Colonoscopy during the
    ⎟ measurement period or the nine years prior to the measurement
    ⎱ period.</NumeratorDescription>

806 ⎰ <ExclusionDescription>Either of the following any time
    ⎟ during the member's history or during the measurement period:
    ⎟ Colorectal cancer or Total colectomy. Deceased patients,
    ⎨ Patients with a hospice encounter, Patients with a skilled
    ⎟ nursing facility encounter or nursing home encounter during
    ⎱ the measurement period.</ExclusionDescription>

<providerRecommendation/>
<patientRecommendation/>
</mdlSummary>
<title>Colorectal Cancer Screening</title>
   <description>The percentage of members 50-75 years of age
who had appropriate screening for colorectal cancer.</
description>

808 ⎰ <defaultTarget>
    ⎟     <targetScore>65</targetScore>
    ⎟     <targetUnit>PERCENT</targetUnit>
    ⎨     <targetDesire>ABOVEOREQUAL</targetDesire>
    ⎟     <targetSource>STAR/PAYOR = 65%</targetSource>
    ⎱ </DefaultTarget>

FIG. 8

```xml
<defaultAttribution>Family_Gastro_Internal_OBGYN_Global</defaultAttribution>
<basePeriod duration="12" durationUnit="MONTHS" xml:id="reporting.period"/>
<referencePeriod periodRef="reporting.period" startOffset="-4" startUnit="YEARS" xml:id="reporting.period.sigmoidoscopy"/>
<referencePeriod periodRef="reporting.period" startOffset="-9" startUnit="YEARS" xml:id="reporting.period.colonoscopy"/>
<everPeriod xml:id="reporting.period.ever"/>
<denominator>
    <cohort evidenceId="1">
        <age evidenceId="2" max="75" min="51" period="reporting.period" periodQual="ON_END_DATE"/>
    </cohort>
</denominator>
<numerator>
    <cohort evidenceId="3">
        <or description="Colorectal Cancer Screening" evidenceId="4">
            <or description="Fecal Occult Blood Test (FOBT)" evidenceId="5">
                <procedure evidenceId="6" snomedIds="104148009|104435004|18433007"/>
                <procedure cptCodes="G0328|82274|82270" evidenceId="7"/>
                <observation evidenceId="8" loincTests="56490-6|27925-7|58453-2|56491-4|2335-8|29771-3|57905-2|27401-9|14563-1|12503-9|14564-9|12504-7|27396-1|27926-5|14565-6"/>
            </or>
            <or description="Sigmoidoscopy" evidenceId="9" period="reporting.period.sigmoidoscopy">
                <procedure evidenceId="10" snomedIds="314607003|425634007|373819004|174172009|112870002|24420007|396226005|44441009|174226004|235338009|18433007|174198003|235342007|174190005"/>
                <procedure evidenceId="11" icdCodes="45.24"/>
                <procedure cptCodes="G0104|45341|45340|45330|45331|45332|45333|45334|45335|45345|45337|45342|45338|45339" evidenceId="12"/>
            </or>
            <or description="Colonoscopy" evidenceId="13" period="reporting.period.colonoscopy">
```

FIG. 9

```
                        <procedure evidenceId="14"
snomedIds="174181003|49870005|174171002|174172009|25732003|184
33007|8180007|373822002|427459009|447021001|57435001|303587008
|443998000|367535003|174180002|444783004|310634005|235150006|4
18714002|12350003|174173004|174184006|235338009|446745002|4465
21004|174158000|73761001|235151005|34264006"/>
                        <procedure evidenceId="15"
icdCodes="45.43|45.25|45.23|0DJD8ZZ|45.42|45.22"/>
                        <procedure
cptCodes="45387|44389|G0105|45386|45379|45378|44397|44388|G012
1|45355|45391|44393|45392|44392|45380|45381|44394|45382|45383|
45384|44391|45385|44390" evidenceId="16"/>
                    </or>
                    <procedure cptCodes="3017F" evidenceId="17"/>
                </or>
            </cohort>
        </numerator>
        <exclusion evidenceId="18">
            <or evidenceId="19">
                <or description="Patient Deceased" evidenceId="20"
period="reporting.period.ever">
                    <deceased evidenceId="21" status="true"/>
                    <diagnosis evidenceId="22"
snomedIds="397709008"/>
                </or>
                <or description="Hospice Encounter"
evidenceId="23">
                    <encounter evidenceId="24"
type="type_hospice"/>
                    <procedure evidenceId="25"
snomedIds="385763009"/>
                    <procedure cptCodes="99378|99377"
evidenceId="26"/>
                </or>
                <or description="Skilled Nursing Facility
Encounter|Nursing Home Encounter" evidenceId="27">
                    <encounter evidenceId="28"
type="type_nursing_home_visit|type_skilled_nursing_facility"/>
                    <diagnosis evidenceId="29"
snomedIds="160734000"/>
                    <procedure
cptCodes="99315|99304|99310|99309|99306|99305|99308|99316|99307"
evidenceId="30"/>
                </or>
```

FIG. 10

```
            <or description="Colorectal Cancer" evidenceId="31"
period="reporting.period.ever">
                <or description="Total Colectomy"
evidenceId="32">
                    <procedure evidenceId="33"
snomedIds="456004|44751009|307666008|31130001|307667004|36192008
|303401008|307669001|80294005|427816007|26390003|235331003"/>
                    <procedure evidenceId="34"
icdCodes="45.83|0DTE0ZZ|45.81|45.8|45.82"/>
                    <procedure
cptCodes="44158|44212|44155|44211|44210|44157|44156|44150|44151|
44152|44153" evidenceId="35"/>
                </or>
                <diagnosis evidenceId="36"
snomedIds="93826009|312114001|285312008|363410008|187757001|1098
38007|93683002|94105000|312111009|269533000|312113007|312115000|
363407001|94072004|93761005|363510005|93771007|363412000|9400600
2|315058005|363406005|312112002|363409003|301756000|363408006|36
3413005"/>
                <diagnosis evidenceId="37"
icdCodes="C18.6|153.8|C18.7|153.7|C18.4|C18.5|153.9|C18.8|C18.9|
153.0|153.2|153.1|153.4|153.3|153.6|V10.05|153.5|153|197.5|C18.3
|154.1|C18.2|154.0|C18.0"/>
                <procedure cptCodes="G0213|G0231|G0215|G0214"
evidenceId="38"/>
            </or>
        </or>
    </exclusion>
</mdl>
```

1102 { (bracket spanning from `<or description="Colorectal Cancer"...` through `</exclusion>`)

FIG. 11

```
----------Patient XXXXXXX
---------Evaluating metadata YYYYYYY
------RefDate 2015-11-23
---Evaluating InitialPatientPopulation
Evaluate: true
Passing Evaluatables: []
Failing Evaluatables: []
Passing Linked Evaluatables: {}
Failing Linked Evaluatables: {}
Evidence: {}
---Evaluating Denominator
Evaluate: true
Passing Evaluatables: [1, 2]
Failing Evaluatables: []
Passing Linked Evaluatables: {}
Failing Linked Evaluatables: {}
Evidence: {EvidenceRecord{record=DemographicPetIndexRecord
[eventDate=Sat Feb 11 00:00:00 EST 1946, conceptId=birth,
ethnicityList=null] BasePetIndexRecord [ageAtEvent=null,
organizationId=64, patId=null, sourceDataType=DEMOGRAPHIC_V2,
ehrSystemId=SOURCE_SYSTEM, isImputed=true,
stdSourceSystemStatus=null, recordIdHash=null] BaseHDto
[rowKey=null, ignoreStatues=null]}=[1, 2]}
---Evaluating Numerator
Evaluate: true
Passing Evaluatables: [3, 4, 13, 14]
Failing Evaluatables: [5, 6, 7, 8, 9, 10, 11, 12]
Passing Linked Evaluatables: {}
Failing Linked Evaluatables: {}
Evidence: {EvidenceRecord{record=ProcedurePetIndexRecord
[encounterRecordId=null, isPrincipal=false, procedureDate=Wed
Mar 12 00:00:00 EST 2010, procedureEndDate=null,
snomedId=73761001, orderStatus=Complete] BasePetIndexRecord
[ageAtEvent=64, organizationId=64, patId=null,
sourceDataType=HEALTH_MAINTENANCE, ehrSystemId=SOURCE_SYSTEM,
isImputed=true, stdSourceSystemStatus=null,
recordIdHash=1211694010] BaseHDto [rowKey=null,
ignoreStatues=null]}=[4, 13, 14, 3]}
---Evaluating Exclusion
Evaluate: false
Passing Evaluatables: []
Failing Evaluatables: [34, 35, 32, 33, 38, 36, 37, 19, 18, 21,
20, 23, 22, 25, 24, 27, 26, 29, 28, 31, 30]
```

FIG. 12

```
       ⎧Passing Linked Evaluatables: {}
1210 ⎨ Failing Linked Evaluatables: {}
       ⎩Evidence: {}
       ⎧---Evaluating Exception
       │Evaluate: false
       │Passing Evaluatables: []
1302 ⎨ Failing Evaluatables: []
       │Passing Linked Evaluatables: {}
       │Failing Linked Evaluatables: {}
       ⎩Evidence: {}
```

FIG. 13

EVIDENCE ANALYSIS AND PRESENTATION TO INDICATE REASONS FOR MEMBERSHIP IN POPULATIONS

BACKGROUND

1. Technical Field

Present invention embodiments relate to tracking, evaluating and analyzing results of conditions applied to data associated with entities, and more specifically, to tracking, evaluating and analyzing conditions to indicate reasons for entities being included/excluded from populations.

2. Discussion of the Related Art

In current systems for evaluating patient populations, conditions associated with population criteria, which is evaluated for each patient, are evaluated as being either true or false and the evaluated conditions and combinations thereof are analyzed to determine whether to include or exclude individual patients with respect to populations for analytics. In order to determine why one or more particular patients are included or excluded from a population, data pertaining to the one or more particular patients must be accessed and analyzed manually to evaluate the conditions and the combinations of conditions that led to the one or more particular patients being either included or excluded from the population. This process is tedious, time-consuming and subject to human error.

SUMMARY

A machine-implemented method, a machine-readable storage medium, and at least one processing device are provided for analyzing and tracking results of multiple conditions associated with a population criteria, which is evaluated for each entity of at least one entity. At least one processing device performs analytics associated with a population criteria evaluated for each entity of at least one entity, wherein each analytic is determined based on a set of conditions. Results of the set of conditions evaluated for each entity of at least one entity are selectively tracked by the at least one processing device. The at least one processing device presents the tracked results to indicate a status of the at least one entity relative to the analytics.

BRIEF DESCRIPTION OF THE DRAWINGS

Generally, like reference numerals in the various figures are utilized to designate like components.

FIGS. 8-11 provide exemplary Measurement Definition Language which may be used in an embodiment.

FIGS. 12-13 show example output with respect to entities and various conditions in an embodiment.

DETAILED DESCRIPTION

A method and system are provided for analyzing and tracking results of multiple conditions associated with a population criteria, which is evaluated for each entity of at least one entity. Analytics may be performed with respect to true or false results of the multiple conditions evaluated for each entity of the at least one entity, which indicate reasons for including each of the at least one entity in or excluding each of the at least one entity from populations for the analytics. In some embodiments, condition results for an entity may be displayed in a visually distinguishable manner, which may include, but not be limited to, color coding, highlighting, or blinking.

In some embodiments, the at least one entity may be one or more patients and conditions may include medical conditions, procedures and office visits.

Figure 1:
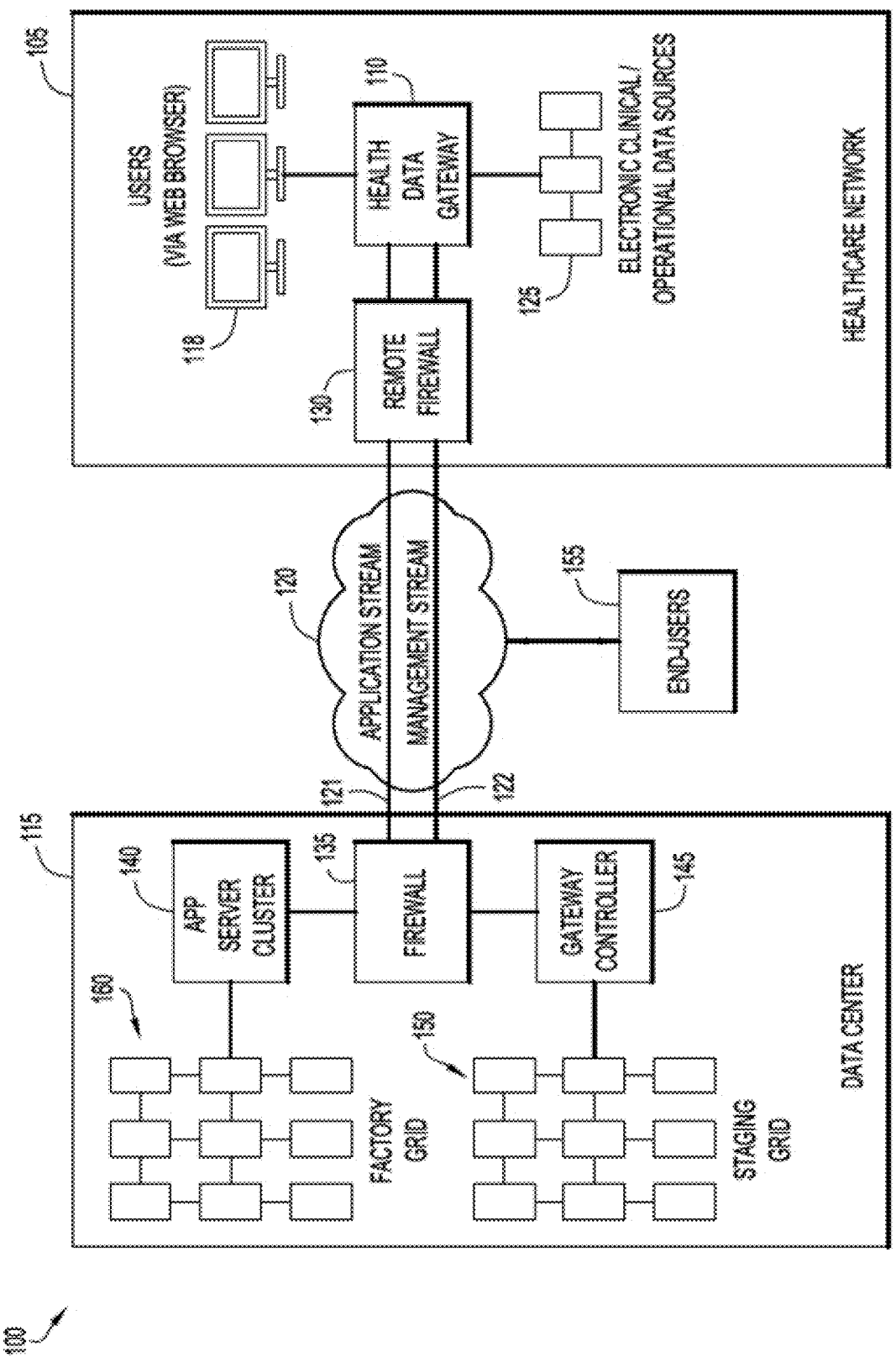
FIG. 1 illustrates an example computing environment for use with present invention embodiments.

An example computing environment for use with present invention embodiments is illustrated in FIG. 1. Computing environment 100 includes a healthcare network 105 in communication with a data center 115 over a communications network 120 (e.g., providing a secure virtual private network (VPN)). The communications over network 120 preferably occur between a firewall 130 of healthcare network 105 and a firewall 135 of data center 115. The communications over network 120 may include an application stream 121 pertaining to communications for applications and a management stream 122 pertaining to communications for managing the data. The network may be implemented by any number of any suitable communications media (e.g., wide area network (WAN), local area network (LAN), Internet, Intranet, etc.). Alternatively, healthcare network 105 and data center 115 may be local to each other, and may communicate via any appropriate local communication medium (e.g., local area network (LAN), hardwired, wireless link, Intranet, etc.).

Healthcare network 105 includes a health data gateway 110 coupled to end-user systems 118 and one or more clinical/operational data sources 125 providing various medical information (e.g., electronic health records (EHR), records from a claims system, lab feed, various data sources implementing the HL7 standard, patient satisfaction survey, etc.) stored according to a source data model.

Data center 115 includes an application server cluster 140, a gateway controller 145, a staging grid 150, and a factory grid 160. Health data gateway 110 of healthcare network 100 is configured to acquire data from data sources 125 and transmit the acquired data to gateway controller 145 of data center 115. The gateway controller receives the incoming data from the communications network and processes that data to staging grid 150. The staging and factory grids each include a cluster of computer systems to store data and perform parallel processing. By way of example, the staging and factory grids each employ a HADOOP cluster with a HADOOP distributed file system (HDFS).

Staging grid 150 inspects and publishes the data to factory grid 160 in accordance with a data model employed by the factory grid. Factory grid 160 includes various engines to perform desired analytics on the data based on queries received from end-user systems 118 and other end-user systems 155 accessing data center 115 over network 120. The queries are handled in conjunction with application server cluster 140 to produce desired results.

Figure 2:
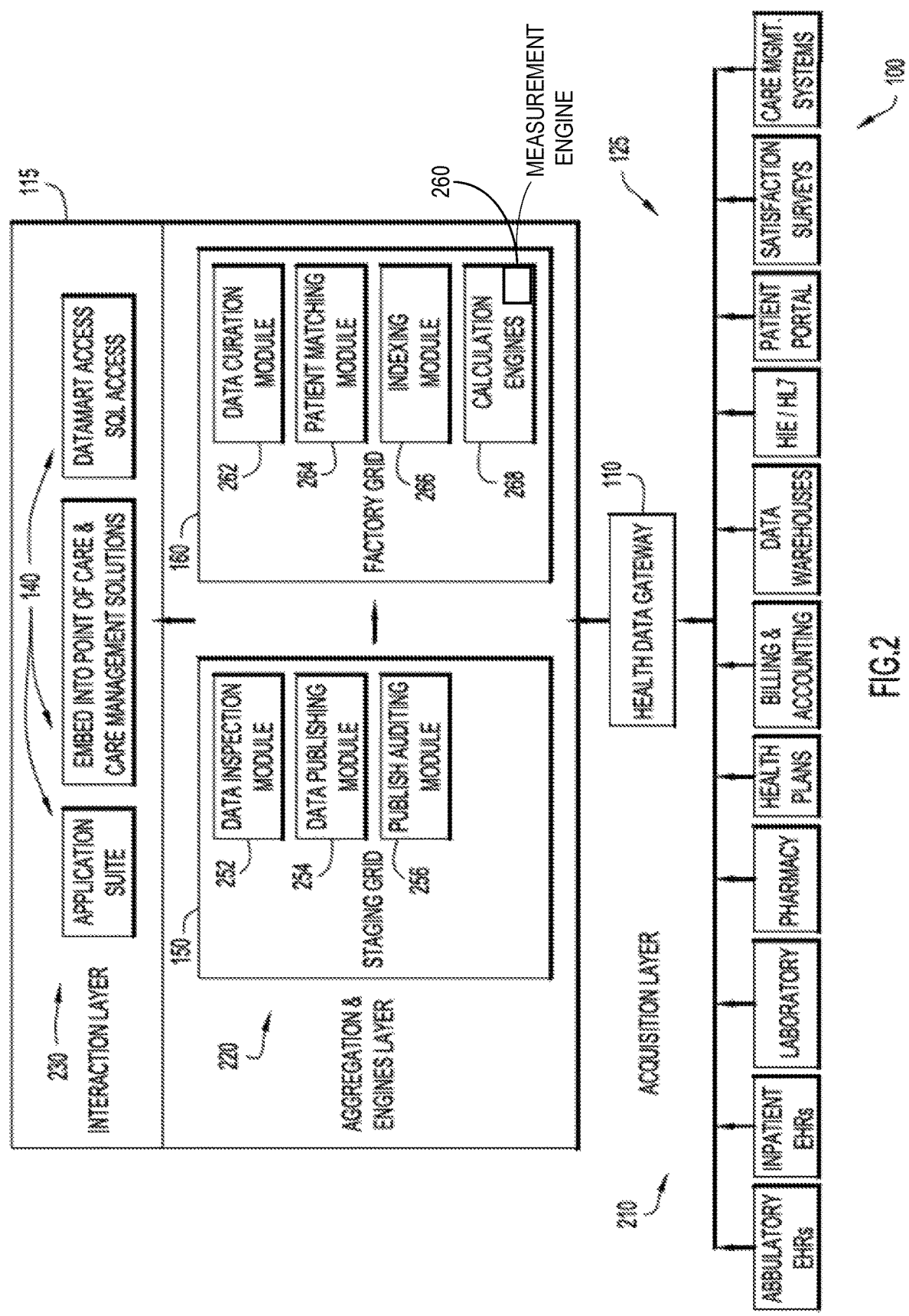
FIG. 2 shows a health data gateway and various layers of data source processing and data center processing.

Referring to FIG. 2, health data gateway 110 of one or more healthcare networks is configured to acquire data from data sources 125 of those healthcare networks (e.g., ambulatory electronic health records (EHR), inpatient electronic health records (EHR), laboratory data, pharmacy data, health plan data, billing and accounting data, data warehouses, health information exchange (HIE)/HL7 data, patient portal, satisfaction surveys, care management systems, etc.) and transmit the acquired data to gateway controller 145 of data center 115 as described above. The healthcare networks and/or data sources 125 form an acquisition layer 210 providing data to data center 115 via health data gateway 110.

Gateway controller 145 receives the incoming data from communications network 120 and processes that data to staging grid 150 employing data models of the source systems. Staging grid 150 includes a data inspection module 252, a data publishing module 254, and a publish auditing module 256 to inspect, publish, and audit the data to factory grid 160 in accordance with the data model employed by the factory grid.

Factory grid 160 includes a data curation module 262, a patient matching module 264, an indexing module 266, and various calculation/analytic engines 268. Data curation module 262 performs data curation operations including mapping codes, data cleansing, and standardization, while patient matching module 264 performs patient matching operations to determine records associated with the same patient. Indexing module 266 performs indexing operations including combining records based on patient matching, mappings, and application of risk models. The calculation/analytic engines, which include measure engine 260 that performs functions for evidence analysis and presentation in various embodiments, perform the desired analytics based on queries received from end-users from an interaction layer 230 enabling application server cluster 140 to provide various applications for processing and accessing the data (e.g., analytic applications, SQL access, etc.). The staging and factory grids form an aggregation and engines layer 220 to process the acquired data, while the queries are handled by factory grid 160 in conjunction with application server cluster 140 to produce desired results for the interaction layer.

The various applications of application server cluster 140 may be provided in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones or other devices, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

Figure 3:
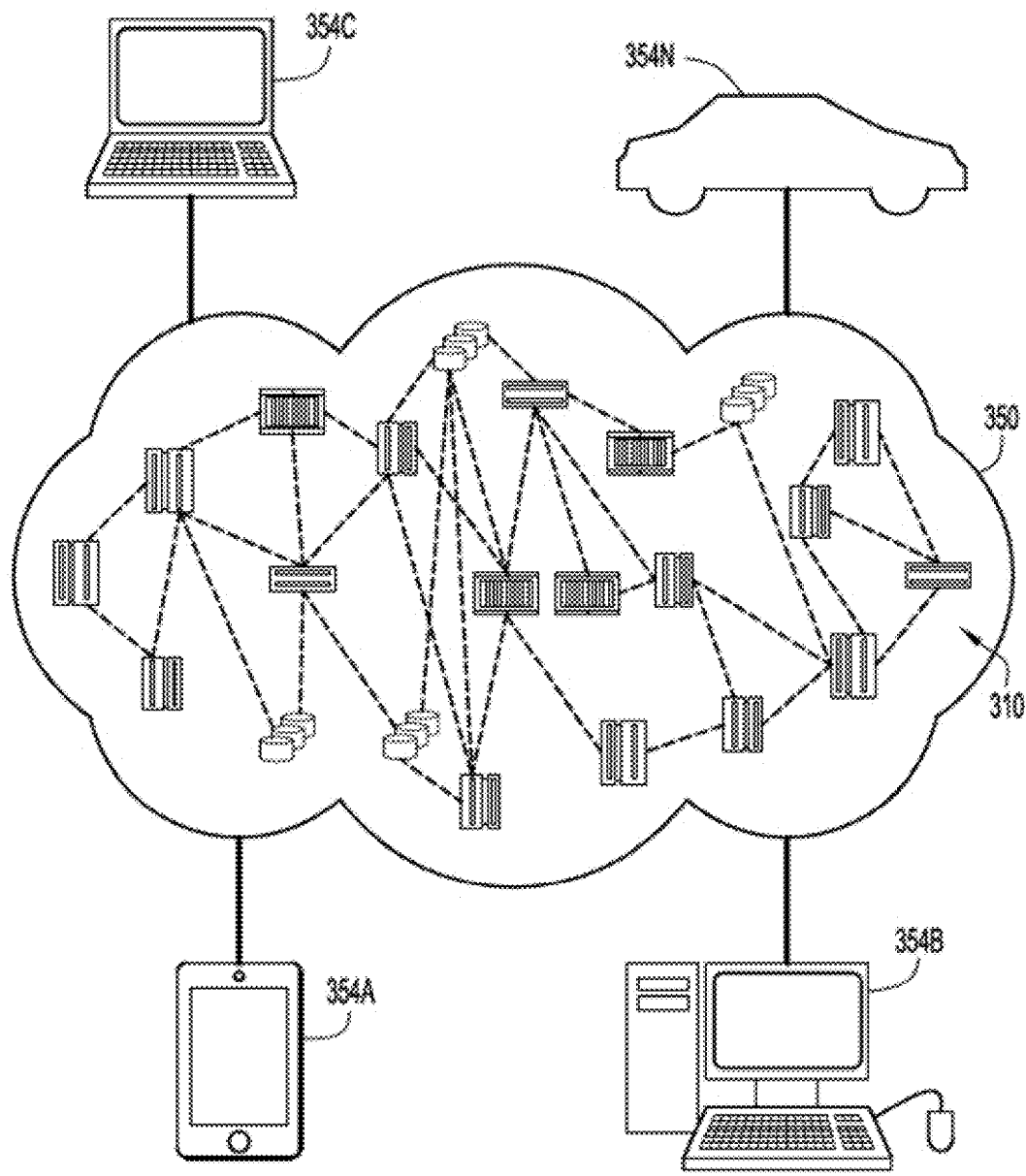
FIG. 3 depicts an illustrative cloud computing environment.

A cloud computing environment is service oriented with a focus on statelessness, low coupling, modularity, and semantic interoperability. At the heart of cloud computing is an infrastructure comprising a network of interconnected nodes. Referring now to FIG. 3, an illustrative cloud computing environment 350 is depicted. As shown, cloud computing environment 350 comprises one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
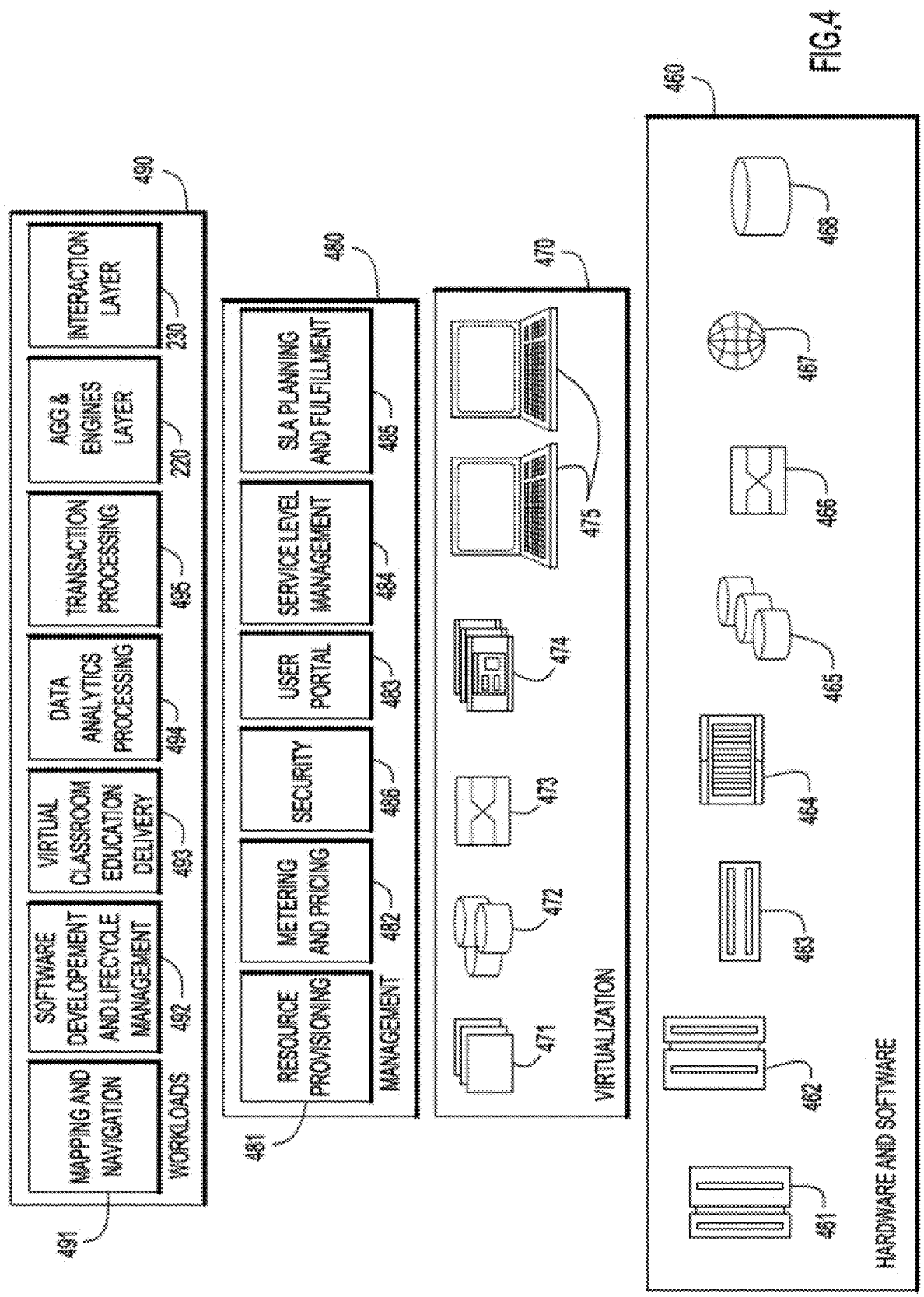
FIG. 4 shows a set of functional abstraction layers provided by a cloud computing environment.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example embodiment, management layer 480 may provide some or all of the functions for data center 115 described herein. Resource provisioning 481 provides dynamic procurement of computing resources and other resources that are utilized to perform tasks within the cloud computing environment. Metering and Pricing 482 provide cost tracking as resources are utilized within the cloud computing environment, and billing or invoicing for consumption of these resources. In one example, these resources may comprise application software licenses. Security 486 provides identity verification for cloud consumers and tasks, as well as protection for data and other resources. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; aggregation and engines layer 220 (FIG. 2); and interaction layer 230 (FIG. 2).

Figure 5:
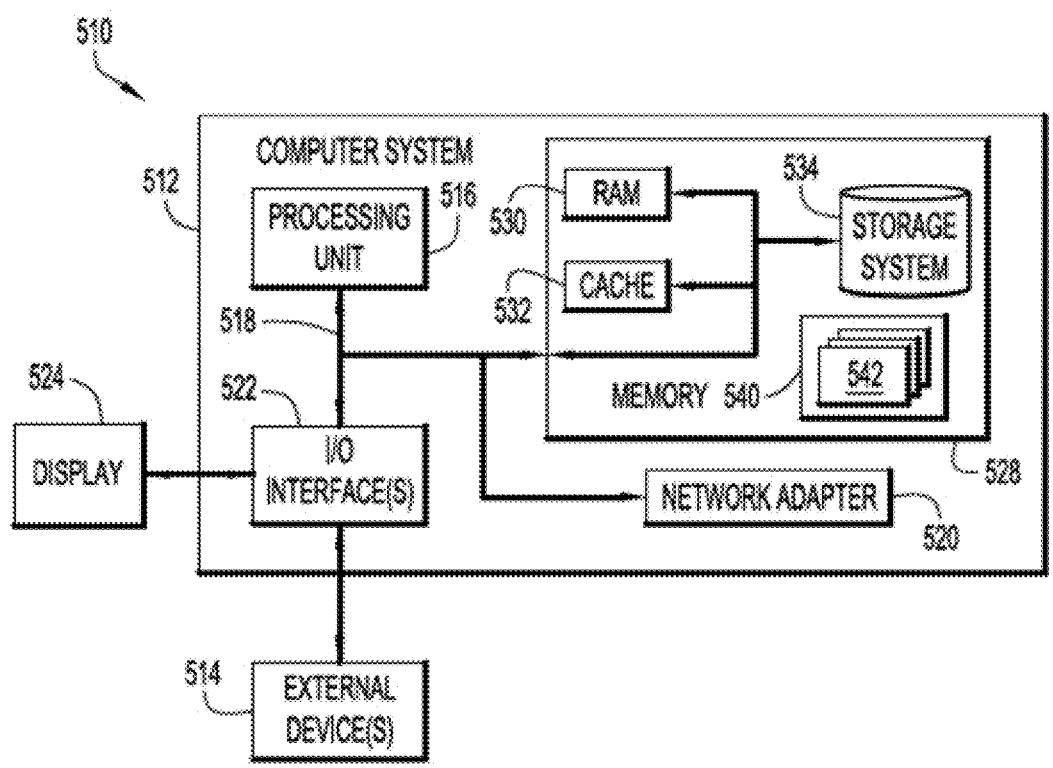
FIG. 5 shows a schematic of an example computing node or device of the computing environment of FIG. 1.

Referring now to FIG. 5, a schematic of an example of a computing node or device 510 of computer environment 100 (e.g., health data gateway 110, application server cluster 140, gateway controller 145, computing nodes of staging grid 150, computing nodes of factory grids 160, etc.) and cloud environment 350 (e.g., cloud computing node 310, etc.) is shown. The computing node or device is only one example of a suitable computing node for computing environment 100 and cloud computing environment 350 and is not intended to suggest any limitation as to the scope of use or functionality of embodiments of the invention described herein. Regardless, computing node 510 is capable of being implemented and/or performing any of the functionality set forth herein.

In computing node 510 there is a computer system 512 which is operational with numerous other general purpose or special purpose computing system environments or configurations. Examples of well-known computing systems, environments, and/or configurations that may be suitable for use with computer system 512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 512 may be described in the general context of computer system executable instructions, such as program modules, being executed by a computer system. Generally, program modules may include routines, programs, objects, components, logic, data structures, and so on that perform particular tasks or implement particular abstract data types. Computer system 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system 512 is shown in the form of a general-purpose computing device. The components of computer system 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 512 typically includes a variety of computer system readable media. Such media may be any available media that is accessible by computer system 512, and it includes both volatile and non-volatile media, removable and non-removable media.

System memory 528 can include computer system readable media in the form of volatile memory, such as random access memory (RAM) 530 and/or cache memory 532. Computer system 512 may further include other removable/non-removable, volatile/non-volatile computer system storage media. By way of example only, storage system 534 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system 512 may also communicate with one or more external devices 514 such as a keyboard, a pointing device, a display 524, etc.; one or more devices that enable a user to interact with computer system 512; and/or any devices (e.g., network card, modem, etc.) that enable computer system 512 to communicate with one or more other computing devices. Such communication can occur via Input/Output (I/O) interfaces 522. Still yet, computer system 512 can communicate with one or more networks such as a local area network (LAN), a general wide area network (WAN), and/or a public network (e.g., the Internet) via network adapter 520. As depicted, network adapter 520 communicates with the other components of computer system 512 via bus 518. It should be understood that although not shown, other hardware and/or software components could be used in conjunction with computer system 512. Examples, include, but are not limited to: microcode, device drivers, redundant processing units, external disk drive arrays, RAID systems, tape drives, and data archival storage systems, etc.

As previously discussed, factory grid 160 includes calculation engines 268 to perform desired analytics based on queries received from end users. In order to perform analytics, calculation engines 268 includes a measurement engine 260 for determining one or more measures for a desired patient population. In various embodiments, a measure may be specified by an XML-type language called Measure Definition Language (MDL), which indicates the criteria for measuring. A measure may include a numerator and a denominator. For example, the denominator may represent a quantity of patients with a particular diagnosis, while the numerator may represent the quantity of patients with the particular diagnosis satisfying a particular condition. However, a measure may include any desired quantity and combinations of conditions for the numerator and denominator.

The MDL for a measure has sections for the denominator and the numerator delineated by tags with each section specifying criteria or conditions for patients to be included within the respective numerator and denominator.

Figure 6:
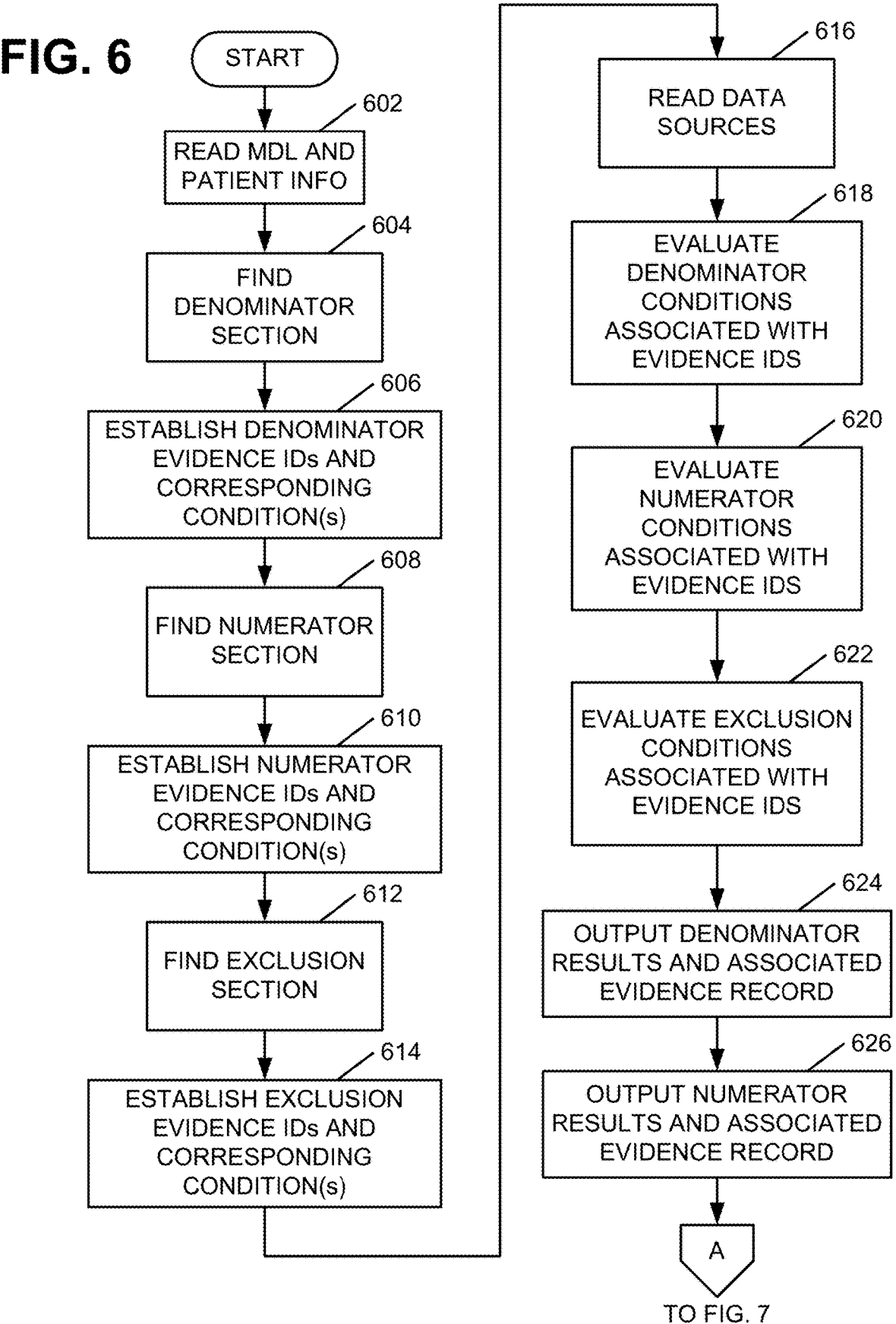
FIGS. 6-7 are flowcharts illustrating example processing that may be performed in various embodiments.
Figure 7:
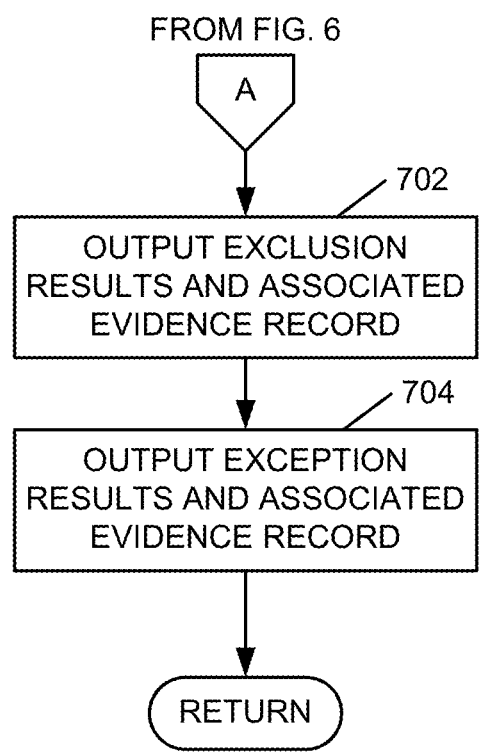

FIGS. 6-7 illustrate exemplary processing with respect to measurement engine 260. The processing illustrated by FIGS. 6-7 assume that evidence IDs and associated conditions are defined in the MDL. The process may begin with measurement engine 260 reading the MDL and information regarding patients of interest (act 602). Measurement engine 260 may then find a denominator section within the MDL (act 604). The denominator section may begin with a tag "<denominator>" and may end with a tag "</denominator>". Denominator evidence IDs and corresponding conditions may then be established as defined in the MDL (act 606).

Next, measurement engine 260 may find a numerator section (act 608). The numerator section may begin with a tag "<numerator>" and may end with a tag "</numerator>". Numerator evidence IDs and corresponding conditions may then be established as defined in the MDL (act 610).

Measurement engine 260 may then find an exclusion section (act 612). The exclusion section may begin with a tag "<exclusion>" and may end with a tag "</exclusion>". In some embodiments, evidence ID information may be included immediately after the word exclusion at a beginning of an exclusion section such as, for example, "<exclusion evidenceId="18">". Exclusion evidence IDs and corresponding conditions may then be established as defined (act 614).

Following the reading of the MDL, measurement engine 260 may then read data sources (act 616), evaluate denominator conditions associated with evidence IDs with respect to the data sources (act 618), evaluate numerator conditions associated with evidence IDs with respect to the data sources (act 620), and evaluate exclusion conditions associated with evidence IDs with respect to the data sources (act 622).

Measurement engine 260 may then output, or present, denominator results and an associated evidence record (act 624). The denominator results may include an indication whether a true denominator condition was found as well as evidence IDs corresponding to the true condition. The associated evidence record, which caused the above-mentioned true denominator condition, may also be output. Thus, by referring to the source MDL and the presented output, one would understand that a patient corresponding to the evidence record satisfied a condition, or conditions, of the denominator and why the patient satisfied the condition, or conditions.

Measurement engine 260 may then output, or present, numerator results and an associated evidence record (act 626). The numerator results may include an indication whether a true numerator condition was found as well as evidence IDs corresponding to the true numerator condition. The associated evidence record, which caused the above-mentioned true numerator condition, may also be output. Thus, by referring to the source MDL and the presented output one would understand that the patient corresponding to the evidence record satisfied a condition, or conditions, of the numerator and why the patient satisfied the condition, or conditions.

Next, measurement engine 260 may output, or present, exclusion results and an associated evidence record (act 702; FIG. 7). The exclusion results include an indication whether a true exclusion condition was found as well as evidence IDs corresponding to the true exclusion condition. The associated evidence record, which caused the above-mentioned true exclusion condition, may also be output. Thus, by referring to the source MDL and the presented output one would understand that the patient corresponding to the evidence record satisfied a condition, or conditions, for exclusion from a population and why the patient satisfied the condition, or conditions.

Measurement engine 260 may then output, or present exception results and an associated evidence record, if any (act 704). An exception occurs when an unexpected condition or error occurs. If an exception occurred, the exception results may indicate that the exception occurred and may include evidence IDs corresponding to a true exception condition. The associated evidence record, which caused the above-mentioned true exception condition, may also be output.

FIGS. 8-11 illustrate example MDL. The MDL includes a denominator description 802 indicating that the denominator includes patients between ages 51-75 years at the end of a measurement. A numerator description 804 indicates that any of the following meet criteria with respect to one or more screenings for colorectal cancer: a fecal occult blood test during the measurement period, a flexible sigmoidoscopy during the measurement period or four years prior to the measurement period, or a colonoscopy during the measurement period or nine years prior to the measurement period. An exclusion description 806 indicates that any of the following any time during a patient's history or during the measurement period would exclude a patient from the population: death, colorectal cancer or total colectomy, a hospice encounter, and a skilled nursing facility encounter or a nursing home encounter during the measurement period. Default target 808 indicates that the target score is ≥65%

$$\left(\text{e.g. } \frac{\text{no. of patients in numerator}}{\text{no. of patients in denominator}} \geq 0.65\right).$$

With reference to FIG. 9, reporting.period.sigmoidoscopy and reporting.period.colonoscopy 902 are defined with respect to a basePeriod 901, which is further defined as having a duration of 12 months and an identifier of reporting.period.

With respect to the denominator 904, evidence ID 1 includes evidence ID 2 regarding conditions of a maximum age of 75 years and a minimum age of 51 years on the end date of the measurement.

With respect to numerator 906, evidence ID 3 is associated with a group of evidence IDs including evidence IDs 4 through 17. "Evidence ID 4 is associated with a set of conditions representing colorectal cancer screening. A colorectal cancer screening can be defined as either a fecal occult blood test (Evidence ID 5), a sigmoidoscopy (Evidence ID 9) or a colonoscopy (Evidence ID 13). Fecal occult blood tests (Evidence ID 5) can be defined using a number of codes, represented by evidence IDs 6, 7, and 8. Evidence ID 6 is associated with SNOMED® (the Systematized Nomenclature of Medicine, is a registered trademark of the International Health Terminology Standards Development Organisation) IDs 104148009, 104435004 and 18433007. Evidence ID 7 is associated with Current Procedure Terminology (CPT) codes G0328, 82274 and 82270. Evidence ID 8 is associated with low income tests 56490-6, 27925-7, 58453-2, 56491-4, 2335-8, 29771-3, 57905-2, 27401-9, 14563-1, 12503-9, 14564-9, 12504-7, 27396-1, 27926-5, and 14565-6. Sigmoidoscopy (Evidence ID 9) can be defined by a number of procedure codes, represented by evidence IDs 10, 11, and 12. Evidence ID 10 is associated with SNOMED® IDs 314607003, 425634007, 373819004, 174172009, 112870002, 24420007, 96226005, 4441009, 174226004, 235338009, 18433007, 174198003, 235342007, and 17490005. Evidence ID 11 is associated with International Classification of Diseases (ICD) code 45.24. Evidence ID 12 is associated with CPT codes G0104, 45341, 45340, 45330, 45331, 45332, 45333, 45334, 45335, 45345, 5337, 45342, 45338, and 45339. Colonoscopy (Evidence ID 13) can be defined by a number of procedure codes, represented by evidence IDs 14, 15, and 16. Evidence ID 14 (FIG. 10) is associated with SNOMED® IDs 174181003, 49870005, 174171002, 174172009, 25732003, 18433007, 8180007, 373822002, 427459009, 447021001, 57435001, 303587008, 443998000, 367535003, 174180002, 444783004, 310634005, 235150006, 418714002, 12350003, 174173004, 174184006, 235338009, 446745002, 446521004, 174158000, 73761001, 235151005, and 34264006. Evidence ID 15 is associated with ICD codes 45.43, 45.25, 45.23, 0DJD8ZZ, 45.42, and 45.22. Evidence ID 16 is associated with CPT codes 45387, 44389, G0105, 45386, 45379, 45378, 44397, 44388, G0121, 45355, 45391, 44393, 45392, 44392, 45380, 45381, 44394, 45382, 45383, 45384, 44391, 45385, and 44390. Evidence ID code 17 is associated with CPT code 3017F.

Exclusion section 1002 includes evidence IDs 18-38, which are associated with excluding a patient from a population. Evidence ID 19 is associated with a group of evidence IDs including evidence IDs 20-38. Evidence ID 20 is associated with two conditions indicating that a patient is deceased, evidence IDs 21 and 22. Evidence ID 21 is associated with a status of being deceased. Evidence ID 22 is associated with a diagnosis having a SNOMED® ID of 397709008. Evidence ID 23 is a group of hospice codes that would cause the patient to be excluded, specifically evidence ID 24, 25 and 26. Evidence ID 24 is associated with a hospice encounter. Evidence ID 25 is associated with a SNOMED® ID of 385763009. Evidence ID 26 is associated with CPT codes 99378 and 99377. Evidence ID 27 is a group of skilled nursing facility or nursing home encounter codes, represented by evidence IDs 28, 29, and 30. Evidence ID 28 is associated with a nursing home visit or skilled nursing facility encounter. Evidence ID 29 is associated with SNOMED® ID 160734000. Evidence ID 30 is associated with CPT codes 99315, 99304, 99310, 99309, 99306, 99305, 99308, 99316, and 99307. Evidence ID 31 (FIG. 11) is a group of codes representing colorectal cancer occurring at any time during the reporting period. Evidence ID 32 is associated with a set of codes representing a total colectomy. Evidence ID 33 is associated with SNOMED® IDs 456004, 44751009, 307666008, 31130001, 307667004, 36192008, 303401008, 307669001, 80294005, 427816007, 26390003, and 235331003. Evidence ID 34 is associated with ICD codes 45.83, 0DTE0ZZ, 45.81, 45.8, and 45.82. Evidence ID 35 is associated with CPT codes 44158, 44212, 44155, 44211, 44210, 44157, 44156, 44150, 44151 and 44152. Evidence ID 36 is associated with SNOMED® IDs 93826009, 312114001, 285312008, 363410008, 187757001, 109838007, 93683002, 94105000, 312111009, 269533000, 312113007, 312115000, 363407001, 94072004, 93761005, 363510005, 93771007, 363412000, 94006002, 315058005, 363406005, 312112002, 363409003, 301756000, 363408006, and 363413005. Evidence ID 37 is associated with ICD codes C18.6, 153.8, C18.7, 153.7, C18.4, C18.5, 153.9, C18.8, C18.9, 153.0, 153.2, 153.1, 153.4, 153.3, 153.6, V10.05, 153.5, 153, 197.5, C18.3, 154.1, C18.2, 154.0, and C18.0. Evidence ID 38 is associated with CPT codes G0213, G0231, G0215, and G0214.

FIGS. 12 and 13 include output for requested patients as a result of evaluating records for the above-described conditions defined by the evidence IDs and tracking the results of each of the conditions. In FIG. 12, when evaluating the denominator, output 1202 indicates that the denominator condition or conditions were satisfied. Output 1204 indicates evidence records that caused the denominator conditions to be satisfied. For example, evidence IDs 1 and 2 evaluated to true due to evidence record 1204. This indicates that a patient's age is between 51 years and 75 years as of the end date of a reporting period.

When evaluating the numerator, output 1206 indicates that the numerator condition or conditions were satisfied. For example, evidence IDs 3, 4, 13 and 14 evaluated to true indicating that the associated patient had a colonoscopy within the reporting period. Evidence IDs 5-12 evaluated to false, indicating that the associated patient did not have a fecal occult blood test or a sigmoidoscopy. Output 1208 shows an evidence record that caused the numerator conditions to be satisfied. For example, the evidence record of output 1208 caused evidence IDs 3, 4, 13 and 14 to be evaluated to true.

Output 1210 relates to excluding a patient from a population. Output 1210 indicates that evidence IDs 34, 35, 32, 33, 38, 36, 37, 19, 18, 21, 20, 23, 22, 25, 24, 27, 26, 29, 28, 31 and 30 evaluated to false and were not true for any evaluated records.

Output 1302 (FIG. 13) indicates that no exception conditions occurred. Exception conditions may be defined as conditions that should not occur. Exception conditions may be associated with evidence IDs. If exception conditions occur, exception output may indicate exception evidence IDs, corresponding to true exception conditions, that evaluated as true and an associated evidence record representative of a patient.

It will be appreciated that the embodiments described above and illustrated in the drawings represent only a few of the many ways of implementing various embodiments. For example, although FIGS. 6-13 are related to conditions defined by MDL, conditions may be defined by other means including, but not limited to, Registry Definition Language (RDL), which may be used to define conditions related to including an entity in or excluding the entity from a registry. When using RDL, the user may define which conditions, when evaluated to true, indicate that a patient is to be included in the registry, and which conditions, when evaluated to true, indicate that the patient is not to be included in the registry. The user may also define exception conditions as described above with respect to RDL.

With respect to MDL, typically multiple populations of entities are measured such as, for example, a numerator, a denominator, an exclusion, etc.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include any information arranged in any fashion, and may be configurable based on rules or other criteria to provide desired information to a user.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

We claim as our invention:

1. At least one machine-readable storage medium having stored therein instructions for respective processors included in respective computer systems of a plurality of computer systems, when the respective processors execute the instructions, the respective processors are configured to perform:
   receiving, by a first plurality of computer systems, electronic entity data associated with a plurality of entities, the electronic entity data being received according to a plurality of different data models, the first plurality of computer systems forming a first computer cluster operating in parallel;
   publishing, by the first plurality of computer systems, the electronic entity data from the plurality of different data models to a data model of a second plurality of computer systems forming a second computer cluster operating in parallel;
   performing, by the second plurality of computer systems, analytics on the published electronic entity data, the performing of the analytics further comprising:
      generating a measure in an XML-type definition language including a plurality of sections indicating criteria for entities to be included in populations used by the measure to perform the analytics,
      inserting evidence ids in the XML-type definition language to associate the evidence ids with the criteria and track evaluation results of each of the criteria for entities to be included in the populations,
      processing the XML-type definition language to perform the measure by:
         finding each respective section based on a respective begin section tag at a beginning of the respective section and a respective end section tag at an end of the respective section,
         establishing for the each respective section one or more evidence ids defined therein, each of the one or more evidence ids corresponding to one or more conditions, each of the one or more conditions having a corresponding time period, the one or more conditions and the corresponding time periods of a first section of the plurality of sections collectively specifying the criteria for entities, associated with the published electronic entity data, to be included in a first population for the performing of the analytics, and the one or more conditions and the corresponding time periods of a second section of the plurality of sections collectively specifying the criteria for entities included in the first population to be included in a second population, which is a subset of the first population,
         determining, based on the published electronic entity data, whether to include in the first population or exclude from the first population each entity of the entities by evaluating, for the each entity, the one or more conditions and the corresponding time periods corresponding to the evidence ids of the first section, each evidence id of the first section being evaluated for the each entity as a result of one of true and false based on results of the evaluating the one or more conditions and the corresponding time periods corresponding to the each evidence id of the first section,
         determining, based on the published electronic entity data, whether to include in the second population or exclude from the second population each entity included in the first population by evaluating the one or more conditions and the corresponding time periods corresponding to the evidence ids defined in the second section, each evidence id of the second section being evaluated for the each entity included in the first population as a result of one of true and false based on results of the evaluating the one or more conditions and the corresponding time periods corresponding to the each evidence id of the second section, and
         tracking the result of the evaluated evidence ids of the first section for the each entity and the result of the evaluated evidence ids of the second section for the each entity included in the first population during processing of the XML-type definition language to perform the measure; and
      presenting, by at least one of the second plurality of computer systems, evidence of evaluation of the evidence ids for the corresponding time periods with respect to the first population and the second population for at least one of the entities.

2. The at least one machine-readable storage medium of claim 1, wherein the conditions include medical conditions.

3. The at least one machine-readable storage medium of claim 2, wherein the tracking further comprises:
tracking results with respect to one or more from a group of specific medical conditions, specific analytics, and specific healthcare providers.

4. The at least one machine-readable storage medium of claim 1, wherein the presenting further comprises:
presenting the result of the evaluated evidence ids of the first and second sections for the at least one of the entities in a visually distinguishable manner.

5. The at least one machine-readable storage medium of claim 1, wherein the plurality of sections includes a denominator section and a numerator section, the denominator section specifying one or more conditions and one or more corresponding time periods for evaluating whether an entity is to be included in a population of the denominator section, and the numerator section specifying one or more conditions and one or more corresponding time periods for evaluating whether the entity is to be included in a population of the numerator section.

6. The at least one machine-readable storage medium of claim 5, wherein the plurality of sections includes an exclusion section specifying one or more conditions and one or more corresponding time periods for excluding an entity from being included in a population.

7. A plurality of processing devices for analyzing and tracking results of a plurality of conditions associated with a population criteria, which is evaluated for each entity of at least one entity, each of the plurality of processing devices comprising:
at least one processor; and
at least one memory connected to one or more of the at least one processor and having instructions stored therein, a first plurality of the processing devices being configured to perform:
receiving electronic entity data associated with a plurality of entities, the electronic entity data being received according to a plurality of different data models, the first plurality of processing devices forming a first computer cluster operating in parallel;
publishing, by the first plurality of the processing devices, the electronic entity data from the plurality of different data models to a data model of a second plurality of the processing devices forming a second computer cluster operating in parallel;
wherein the second plurality of processing devices is configured to perform:
performing analytics on the published electronic entity data, the performing of the analytics further comprising:
generating a measure in an XML-type definition language including a plurality of sections indicating criteria for entities to be included in populations used by the measure to perform the analytics,
inserting evidence ids in the XML-type definition language to associate the evidence ids with the criteria and track evaluation results of each of the criteria for entities to be included in the populations,
processing the XML-type definition language to perform the measure by:
finding each respective section based on a respective begin section tag at a beginning of the respective section and a respective end section tag at an end of the respective section,
establishing for the each respective section one or more evidence ids defined therein, each of the one or more evidence ids corresponding to one or more conditions, each of the one or more conditions having a corresponding time period, the one or more conditions and the corresponding time periods of a first section of the plurality of sections collectively specifying the criteria for entities, associated with the published electronic entity data, to be included in a first population for the performing of the analytics, and the one or more conditions and the corresponding time periods of a second section of the plurality of sections collectively specifying the criteria for entities included in the first population to be included in a second population, which is a subset of the first population,
determining, based on the published electronic entity data, whether to include in the first population or exclude from the first population each entity of the entities by evaluating, for the each entity, the one or more conditions and the corresponding time periods corresponding to the evidence ids of the first section, each evidence id of the first section being evaluated for the each entity as a result of one of true and false based on results of the evaluating the one or more conditions and the corresponding time periods corresponding to the each evidence id of the first section,
determining, based on the published electronic entity data, whether to include in the second population or exclude from the second population each entity included in the first population by evaluating the one or more conditions and the corresponding time periods corresponding to the evidence ids defined in the second section, each evidence id of the second section being evaluated for the each entity included in the first population as a result of one of true and false based on results of the evaluating the one or more conditions and the corresponding time periods corresponding to the each evidence id of the second section, and
tracking the result of the evaluated evidence ids of the first section for the each entity and the result of the evaluated evidence ids of the second section for the each entity included in the first population during processing of the XML-type definition language to perform the measure; and
presenting, by at least one of the second plurality of processing devices, evidence of evaluation of the evidence ids for the corresponding time periods with respect to the first population and the second population for at least one of the entities.

8. The plurality of processing devices of claim 7, wherein the conditions include medical conditions.

9. The plurality of processing devices of claim 7, wherein the plurality of sections includes a denominator section and a numerator section, the denominator section specifying one or more conditions and one or more corresponding time periods for evaluating whether an entity is to be included in a population of the denominator section, and the numerator section specifying one or more conditions and one or more corresponding time periods for evaluating whether the entity is to be included in a population of the numerator section.

10. The plurality of processing devices of claim 9, wherein the plurality of sections includes an exclusion section specifying one or more conditions and one or more corresponding time periods for excluding an entity from being included in a population.

\* \* \* \* \*